United States Patent [19]
Akazawa

[11] Patent Number: 5,911,742
[45] Date of Patent: *Jun. 15, 1999

[54] ATTACHMENT TO AIR-CONDITIONER

[76] Inventor: Yasumasa Akazawa, 2-18-14, Higashishinmachi, Matsubara, Osaka, Japan

[*] Notice: This patent is subject to a terminal disclaimer.

[21] Appl. No.: 08/901,443

[22] Filed: Jul. 28, 1997

[51] Int. Cl.⁶ .............................. C01F 1/00; C01G 15/00; F24F 3/16
[52] U.S. Cl. .................. 62/78; 62/303; 62/237; 422/123; 422/124; 165/41
[58] Field of Search ........................ 62/78, 303; 422/123; 165/41

[56] References Cited

U.S. PATENT DOCUMENTS

| | | | |
|---|---|---|---|
| 4,303,617 | 12/1981 | Bryson | 422/123 |
| 5,429,180 | 7/1995 | Nishino et al. | 165/41 |
| 5,664,423 | 9/1997 | Akazawa | 62/303 |

*Primary Examiner*—Henry Bennett
*Assistant Examiner*—Melvin Jones
*Attorney, Agent, or Firm*—Moonray Kojima

[57] ABSTRACT

The present invention relates to an attachment to an air-conditioner for cooling and heating the room in ordinary home, office, factory, shop, etc., being an attachment to an air-conditioner disposing at least one solvent discharge means in an air-conditioning channel between an air suction portion and an air blow-out portion, wherein at least one solvent of cleaning, aromatic, antimicrobial, deodorant or anti-mold effect, or a compound solvent is discharged from the solvent discharge means, so that the cleaning, aromatic, antimicrobial, deodorant or anti-mold effect may be obtained depending on the solvent being used, thereby improving the indoor environments.

8 Claims, 12 Drawing Sheets

ATTACHMENT TO AIR-CONDITIONER

BACKGROUND OF THE INVENTION

1. Field of the Invention

The present invention relates to an attachment to an air-conditioner for cooling and heating the room in ordinary home, office, factory, shop, etc.

2. Description of the Prior Art

Hitherto, the air-conditioner comprises a heat exchanger in its housing which functions as an evaporator when cooling and as a condenser when heating, and since heat is exchanged in the indoor air containing dust, moisture, cigarette smoke or the like from the air suction portion provided in the housing, fins of complicated shape of the heat exchanger are likely to be contaminated and grow germs and molds.

When the air-conditioner is operated in such state, the indoor sanitation is impaired, and offensive smell is generated to deteriorate the indoor environments.

SUMMARY OF THE INVENTION

It is hence an object of the invention to present an attachment to an air-conditioner capable of obtaining cleaning, aromatic, antifungal, deodorizing, and anti-mold effects and enhancing the indoor environments by the solvent discharge from solvent discharge means, by disposing at least one solvent discharge means in the air-conditioning channel between the air suction portion (including both air suction port and air suction duct) and air blow-out portion.

It is other object of the invention to present an attachment to an air-conditioner capable of offering effective cleaning, antifungal, deodorizing and anti-mold effects to the heat exchanger that is most likely to be contaminated, and releasing aroma into the room, by disposing solvent discharge means at the upstream side (windward side) from the heat exchanger.

It is a different object of the invention to present an attachment to an air-conditioner capable of enhancing the controllability of the solvent from a solvent source, without sacrificing the appearance of the air-conditioner and the building, by disposing means communicating with solvent discharge means and receiving solvent from the solvent source, on the outer surface of the air-conditioner or on indoor side of the building.

Other objects of the invention will be better understood from the following detailed description of the embodiments.

DESCRIPTION OF THE PREFERRED EMBODIMENTS

Referring now to the drawings, embodiments of the invention are described in detail below.

Figure 1:
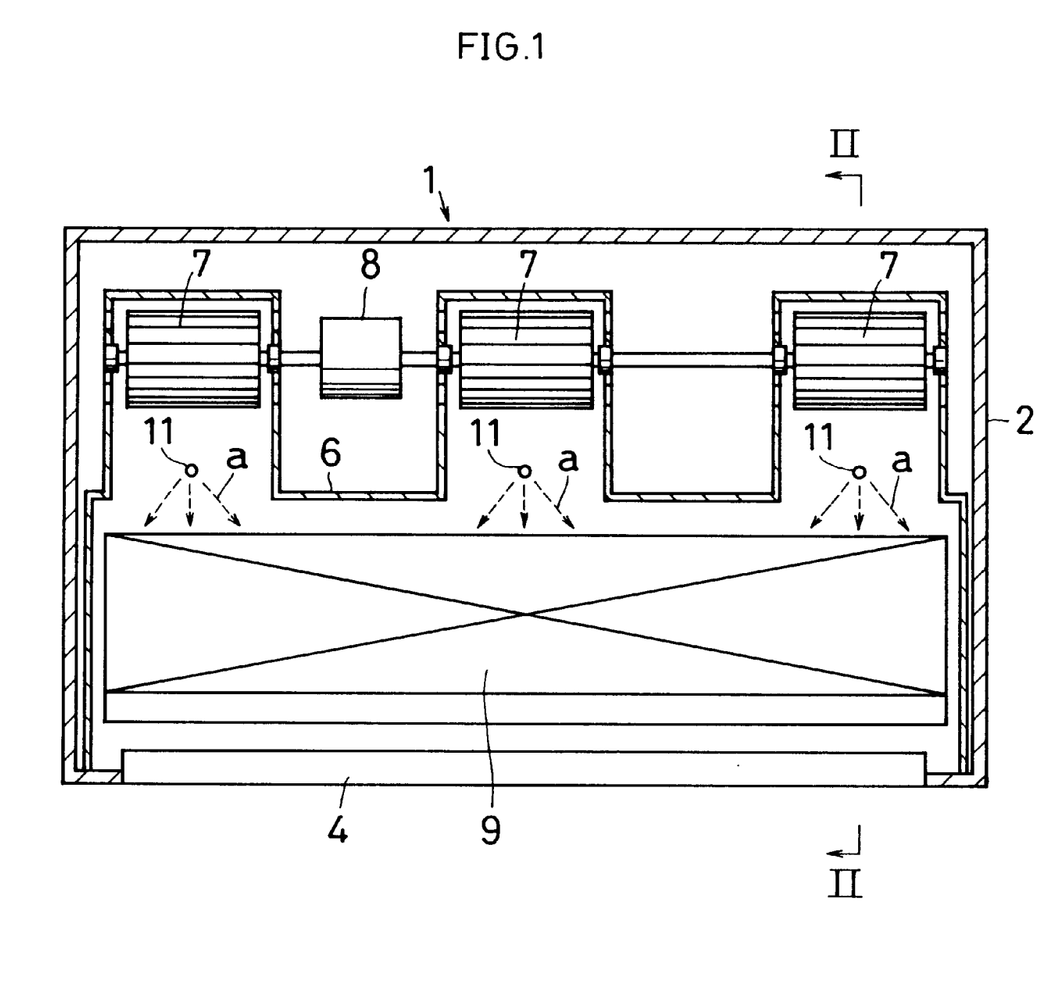
FIG. 1 is a sectional view showing an attachment to a ceiling suspension type air-conditioner of the invention.
Figure 2:
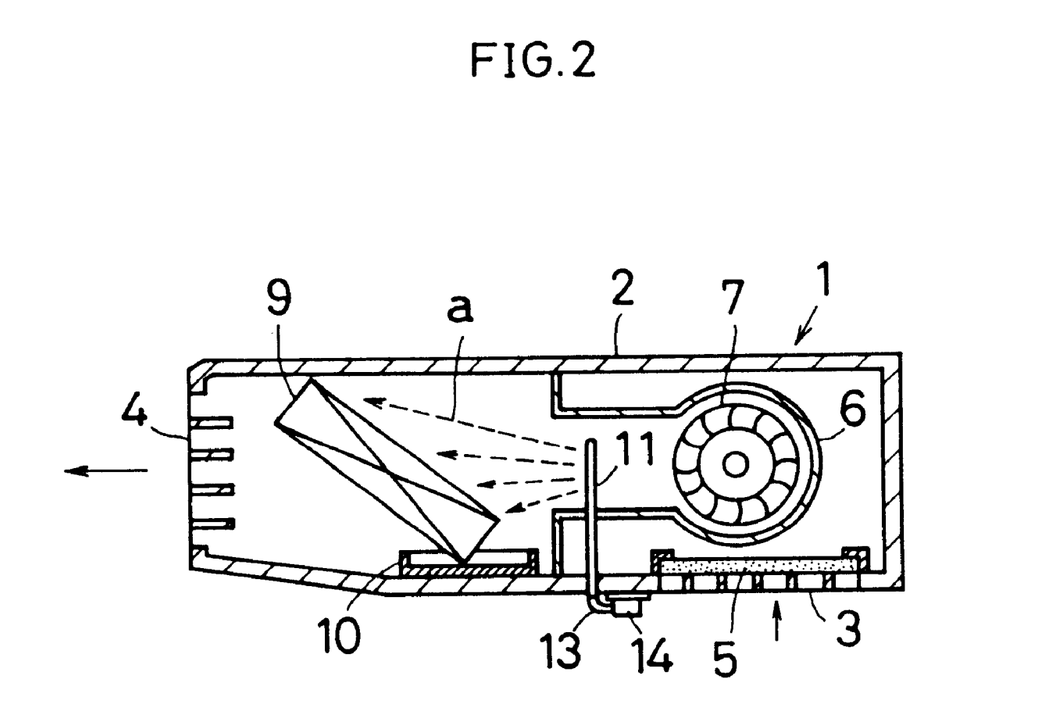
FIG. 2 is a sectional view of II–VI line arrow in FIG. 1.

The drawings show an attachment to an air-conditioner, and in FIG. 1 and FIG. 2, in a ceiling suspension type air-conditioner 1, an air suction port 3 and an air blow-out port 4 are formed at one side and other side of a housing 2, and a filter 5 is detachably formed inside the air suction portion 3.

At the wind blowing side in the housing 2, three fans 7 (wind blowing means) enclosed by a fan casing 6 are disposed, and it is constituted to drive the three fans 6 by one motor 8, and a heat exchanger 9 is disposed between the discharge side of the fans 7 and the air blow-out port 4, and a drain pan 10 is disposed at the lower end of the heat exchanger 9. The heat exchanger 9 is connected to a refrigeration cycle, and functions as an evaporator when cooling and as a condenser when heating.

In thus constituted air-conditioner 1, as an example of air-conditioning channel between the air suction port 3 and the air blow-out port 4, a nozzle 11 (solvent discharge means) is set up from the lower part of the housing 2 so that the solvent discharge portion (an ejection port 12 in FIG. 3) may be located between the upstream side of the heat exchanger and the downstream side of the fans 7.

Figure 3:
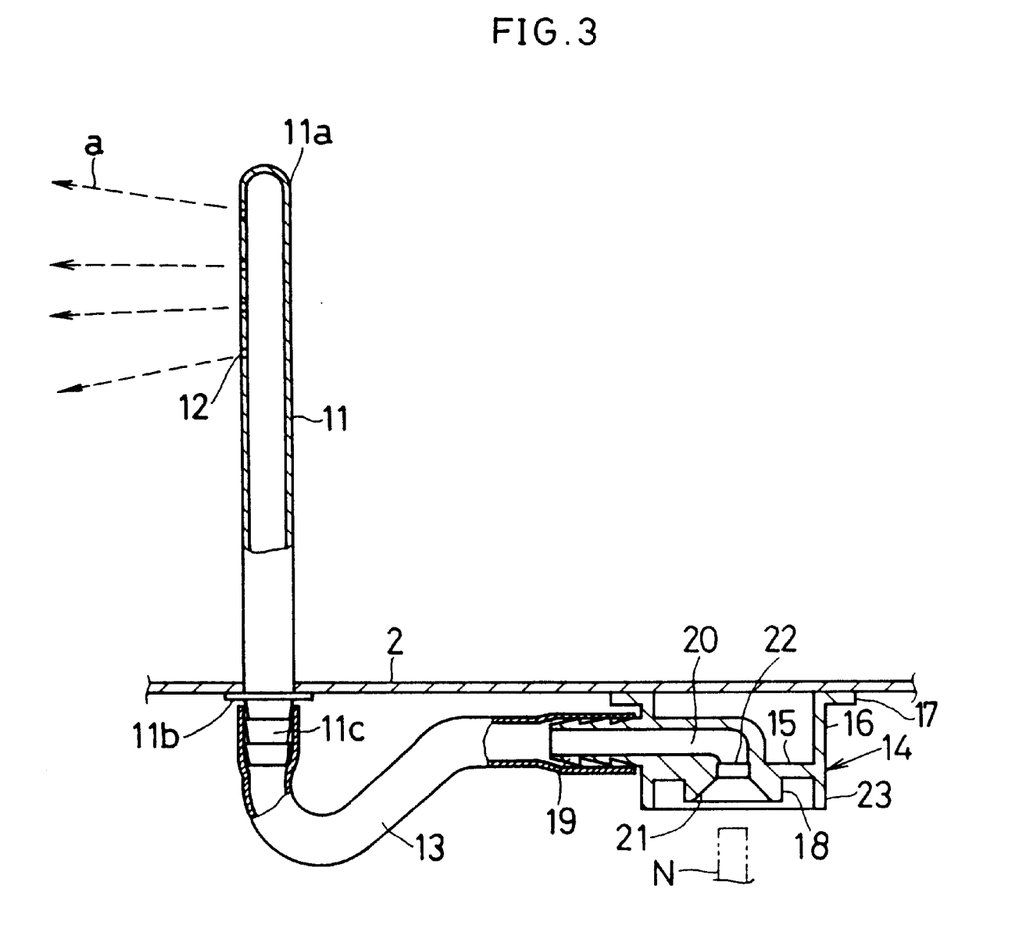
FIG. 3 is an essential magnified view of FIG. 2.

A total of three nozzles 11 are nearly identical in structure, and the specific structure is as shown in FIG. 3. That is, the nozzle 11 is a relatively slender cylindrical form with its leading end 11a closed, and at the location confronting the front side of the heat exchanger 9, plural ejection ports 12 for ejecting a solvent fluid a in the dotted line arrow direction in FIG. 1 to FIG. 3 are pierced. If necessary, meanwhile, the ejection ports 12 may be formed at the fan 7 side of the nozzle 11.

At the basal end side of the nozzle 11, a flange 11b and a joint 11c are provided, and the flange 11b is joined to the outer surface of the housing by proper means (adhesive, clip, bolt, etc.), and the leading end side of a rubber hose 13 (solvent feed route) is fitted and fixed to the joint 11c by making use of its elastic tightening force. Instead of the rubber hose 13, a resin tube or metal piping may be used.

Moreover, on the same outer surface of the housing 2 near the joint 11c of the nozzle 11, a receiving member 14 (receiving means) made of synthetic resin is fixed by proper means (joining by adhesive, bolt, clip, or both-side adhesive tape).

In the receiving member 14, a flange 17 is integrally formed through a ring-shaped spacer 16 in a principal plate 15 positioned in the middle, and a solvent passage 20 is formed between a guide 18 provided in the center of the principal plane 15 and a joint 19 projection outward from a part of the outer circumference of the spacer 16.

The guide 18 is to position the nozzle N of the filling container A (a handy type solvent container packed with gas; see FIG. 9) when supplying the solvent, and a taper 21 for guiding the nozzle larger in diameter at the outer side and smaller in diameter at the inner side is formed in the guide 18. At the inner side of the taper 21, an annular step 22 for preventing excessive insertion of the nozzle N is formed. Meanwhile, a lid member (not shown) may be detachably supported on a holder 23 integrally formed at the anti-spacer side in the principal plate 15.

In the joint 19 of the receiving member 14, the basal end side of the rubber hose 13 is fitted and fixed by making use of its elastic tightening force, and the solvent passage 20 of the receiving member 14 communicates with the nozzle 11 through the rubber hose 13. Herein, rubber hoses 13 and receiving members 14 may be independently provided in three nozzles shown in FIG. 1, or it may be constituted so that the solvent fluid may be supplied simultaneously from one receiving member 14 to three nozzles 11.

Usable examples of the solvent fluid a include liquid detergent, foamed detergent (blending proper amount of water, phosphoric acid, Softanol 70, propylene glycol monoethyl ether, MFG, etc.), cleaning water, aromatic material, chemical, deodorant, antifungal, anti-mold, and others alone or in mixture (complex).

Elements 11, 13, 14 shown in FIG. 3 may be handled as kit, and the elements 11, 13, 14 may be attached later to the air-conditioner 1, or may be mounted integrally in advance when manufacturing the air-conditioner 1.

In thus constituted attachment to the air-conditioner, the operation is described below.

When cleaning the heat exchanger 9, the nozzle N of the filling container A is inserted into the solvent passage 20 while guiding by the taper 21 of the guide 18 in the receiving member 14, and the cleaning fluid is sent under pressure from the nozzle N. The cleaning fluid is supplied into the rubber hose 13 through the solvent passage 20, and flows into the nozzle 11 from its leading end, and is ejected from the multiple ejection ports 12 toward the nearly entire front region of the heat exchanger 9. Therefore, fins (not shown) of complicated shape of the heat exchanger 9 can be cleaned well almost entirely. The fluid after cleaning process is discharged from the drain pan 10 immediately beneath the heat exchanger 9 through the drain line. If necessary, meanwhile, the fluid after cleaning process may be discharged from the air blow-out port 4, and this fluid may be stopped by proper means.

Herein, when the fan 7 is driven while ejecting cleaning fluid from the ejection port 12, the cleaning fluid reaches further inside of the fins of complicated shape of the heat exchanger 9, so that the cleaning effect may be enhanced further.

Incidentally, the sequence of use of cleaning fluid 1 may be any one of the sequence of foamed detergent and chemical (bactericidal, etc.), the sequence of foamed detergent, cleaning water, and chemical, or the sequence of non-foam liquid detergent and bactericidal, and after the cleaning process, moreover, the heat exchanger 9 may be dried by supplying air, warm air, hot air, or cold air from the basal end opening side of a rubber hose 13.

In particular, when the solvent fluid a ejected from the nozzle 1 is set in foamed cleaning fluid, if the dimension of the nozzle 11 is relatively short, the foamed cleaning fluid ejected from the nozzle 11 spreads widely in the entire front region (that is, all surface) of the upstream side of the heat exchanger 9, so that the entire heat exchanger 9 can be cleaned efficiently to the inner parts by the foamed cleaning fluid by the wind pressure from the fan 7, so that it is effective to form the nozzle 11 in small and compact design, and enhance the mounting performance of the nozzle 11 on the air-conditioner 1.

Instead of cleaning of the heat exchanger 9, to apply antifungal, deodorizing or anti-mold treatment on the heat exchanger 9, a nozzle N of a filling container A packed with a corresponding solvent may be inserted into a specified position of the receiving member 14, and the corresponding solvent may be sent out under pressure. Or, to release aroma into the room by making use of the air-conditioning wind, a filling container A packed with an aromatic solvent may be similarly operated.

In this way, at least one solvent discharge means (nozzle 11) is disposed in the air-conditioning channel, the cleaning, aromatic, antifungal (including decontaminant, antimicrobial and bactericidal), or deodorant (including odor preventive and odor removing) effect or anti-mold effect may be obtained corresponding to the solvent discharged from the solvent discharge means (nozzle 11), so that the indoor environments may be enhanced.

Besides, since the solvent discharge means (nozzle 11) is disposed at the upstream side of the heat exchanger 9, effective cleaning, antimicrobial, deodorizing or anti-mold treatment can be applied nearly on the entire fins of complicated shape of the heat exchanger 9, and also aroma can be released into the room by making use of the air-conditioning wind.

Further, communicating with the solvent discharge means (nozzle 11), means for receiving solvent (receiving member 14) from the solvent source (filling container A) is provided on the outer surface of the air-conditioner 1, so that the controllability of supply of solvent from the solvent source can be enhanced without sacrificing the appearance of the air-conditioner. That is, only by inserting the nozzle N of the filling container A into the guide 18 of the receiving member 14 by one-touch operation, the corresponding solvent can be ejected from the nozzle 11.

The nozzle 11 may be directed to the suction portion of the centrifugal fan 7, or when the nozzle 11 is disposed at the upstream side of the fan 7, it is effective to treat not only the heat exchanger but also the fan blades of complicated shape by various solvents. The nozzles 11 may be also disposed at both upstream side of the heat exchanger 9 and upstream side of the fan 7. When releasing the aromatic solvent, the nozzle 11 may be disposed at any position between the air suction port 3 and air blow-out port 4.

Figure 4:
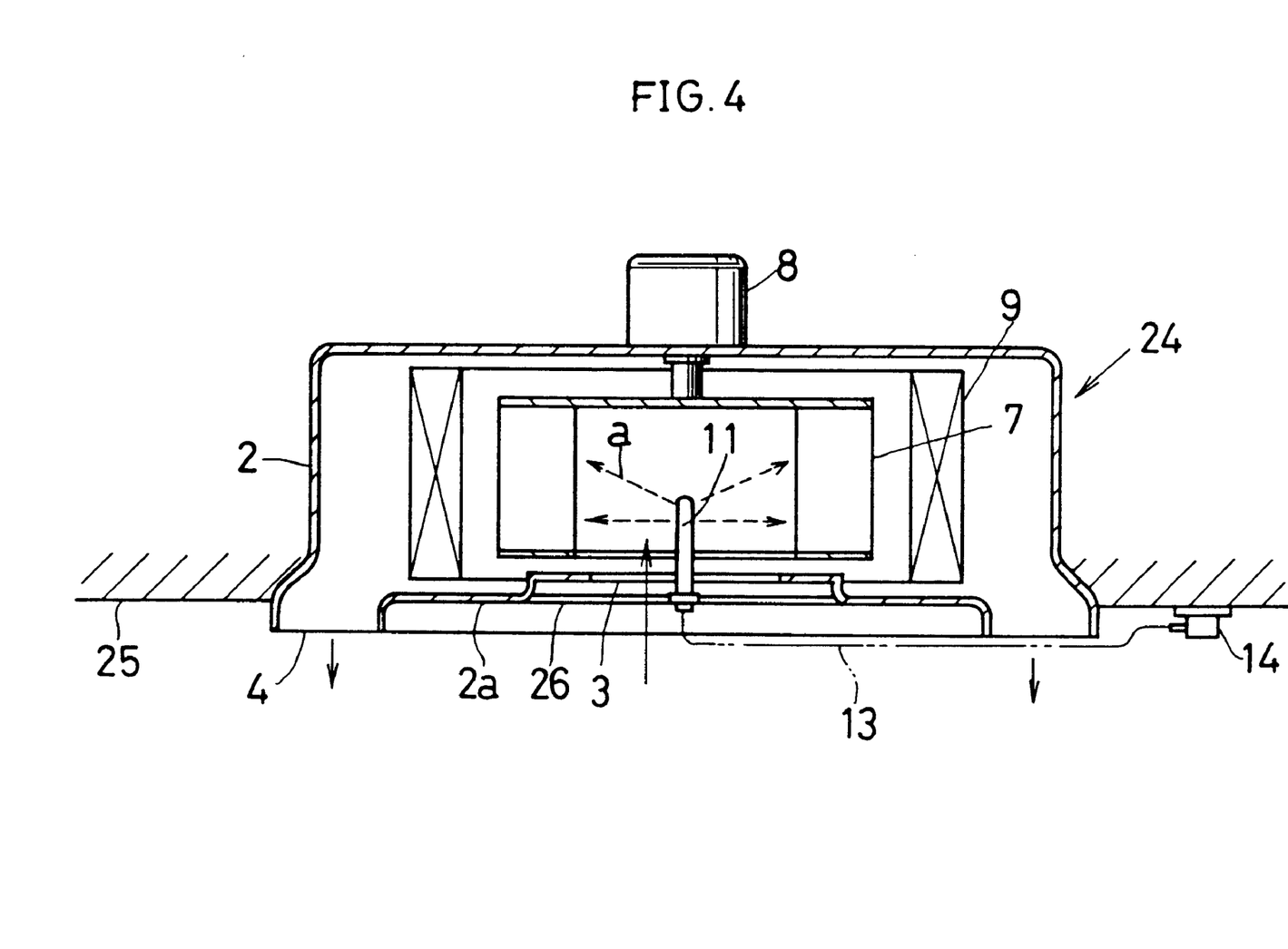
FIG. 4 is a sectional view showing an attachment to a ceiling buried type air-conditioner of the invention.

Other embodiments are shown in FIG. 4 through FIG. 12, and in these drawings same reference numbers are given to corresponding parts and detailed description is omitted. FIG. 4 is an embodiment applied to a ceiling buried type air-conditioner 24, wherein the air-conditioner 24 is buried in a ceiling 25, and the air blow-out port 4 is formed on the outer circumference of the air suction port 3, and the heat exchanger 4 formed nearly in an annular shape is disposed on the outer circumference of the centrifugal fan 7.

In this kind of air-conditioner 24, the nozzle 11 is disposed to be positioned in the center of the fan 7 in a housing lower part 2a exposed to the indoor side through a support member 26 (support means), a receiving member 14 is disposed in the housing lower part 2a or at the lower side of the ceiling 25, and the both members 11, 114 are connected to communicate through a rubber hose 13 or a proper piping.

Alternatively, the receiving member 14 may be attached to the indoor side of the vertical wall of the building, and the receiving member 14 is located at a close position easy for manipulation of solvent supply, and the receiving member 14 and nozzle 11 may by connected through a solvent supply route (rubber hose 13, resin tube, metal piping, etc.).

In this constitution, by the centrifugal suction force by rotation of the fan 7, cleaning, antimicrobial, deodorizing or anti-mold treatment can be applied nearly to the entire fan blades and heat exchanger 9 most efficiently by various solvents ejected from the ejection port 12 (see FIG. 12) of the nozzle 11, and when an aromatic solvent is used, aroma is released into the room. The location of the nozzle 11 may be also a position confronting a lower position of the fan blades disposed in an annular form. In this constitution, the same actions and effects as in the preceding embodiment are obtained.

Figure 5:
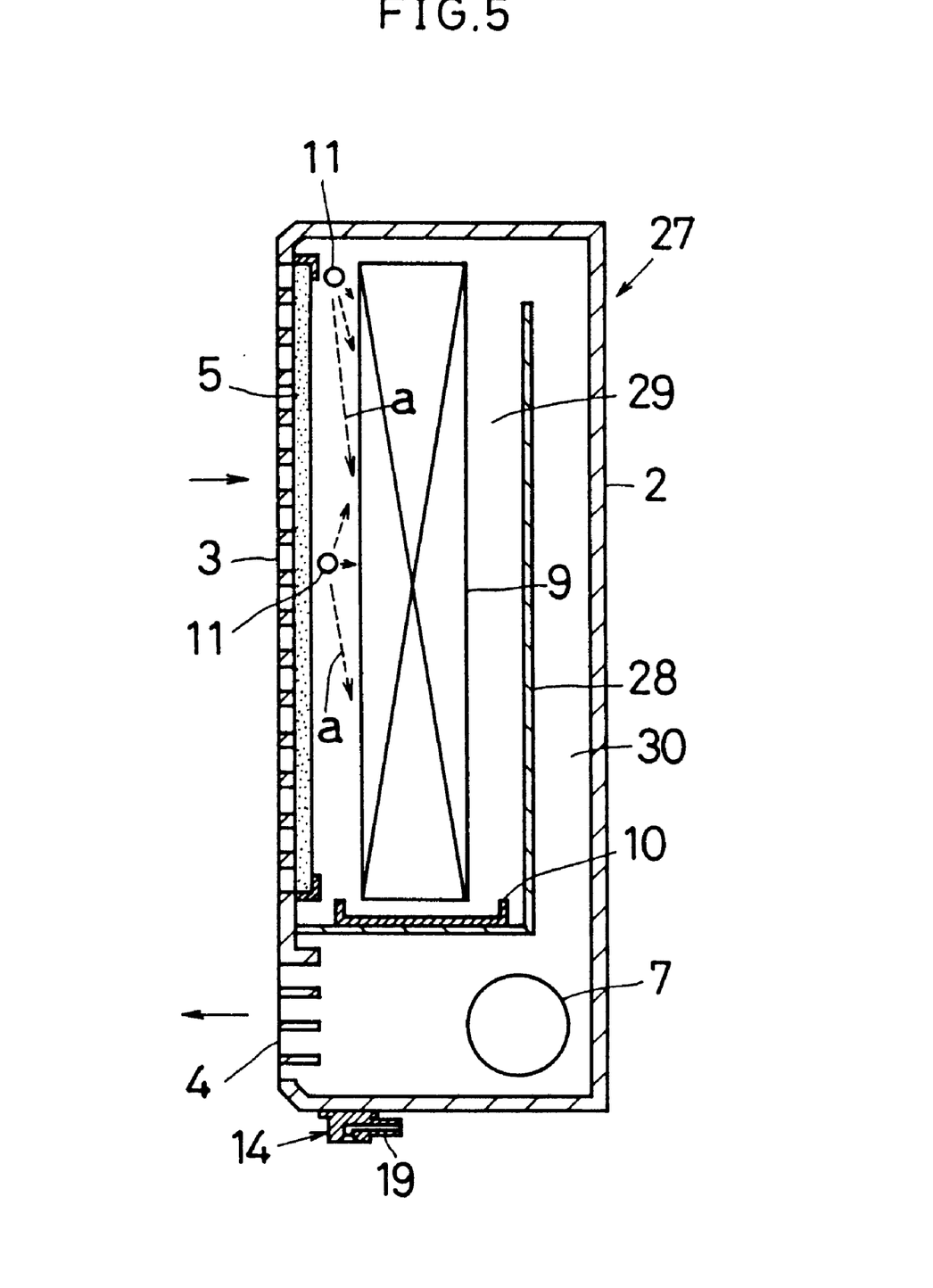
FIG. 5 is a sectional view showing an attachment to a wall mount type air-conditioner of the invention.

FIG. 5 shows an embodiment applied to a wall mount type air-conditioner 27, in which a receiving member 14 and communicating two nozzles 11 are disposed horizontally between the front side (upstream side) of the heat exchanger 9 and the back side of the filter 5 at the upstream side of the heat exchanger 9.

Of the two nozzles 11, at least the nozzle 11 position at the upper side has a length equivalent to the overall width of the heat exchanger 9. In particular, when a foamed (mousse) cleaning fluid is used as the solvent, the foamed cleaning fluid is sprayed from the upper nozzle 11 to spread over the entire heat exchanger 9, and the foamed cleaning fluid flowing downward is sucked by the fan 7 through passages 29, 30 divided by a partition member 28, and the foamed cleaning fluid after cleaning is released and discharged from the air blow-out port 4, and the entire heat exchanger 9 and fan 7 can be efficiently cleaned. In this constitution, too, in other points, nearly same actions and effects as in the foregoing embodiments are obtained.

Figure 6:
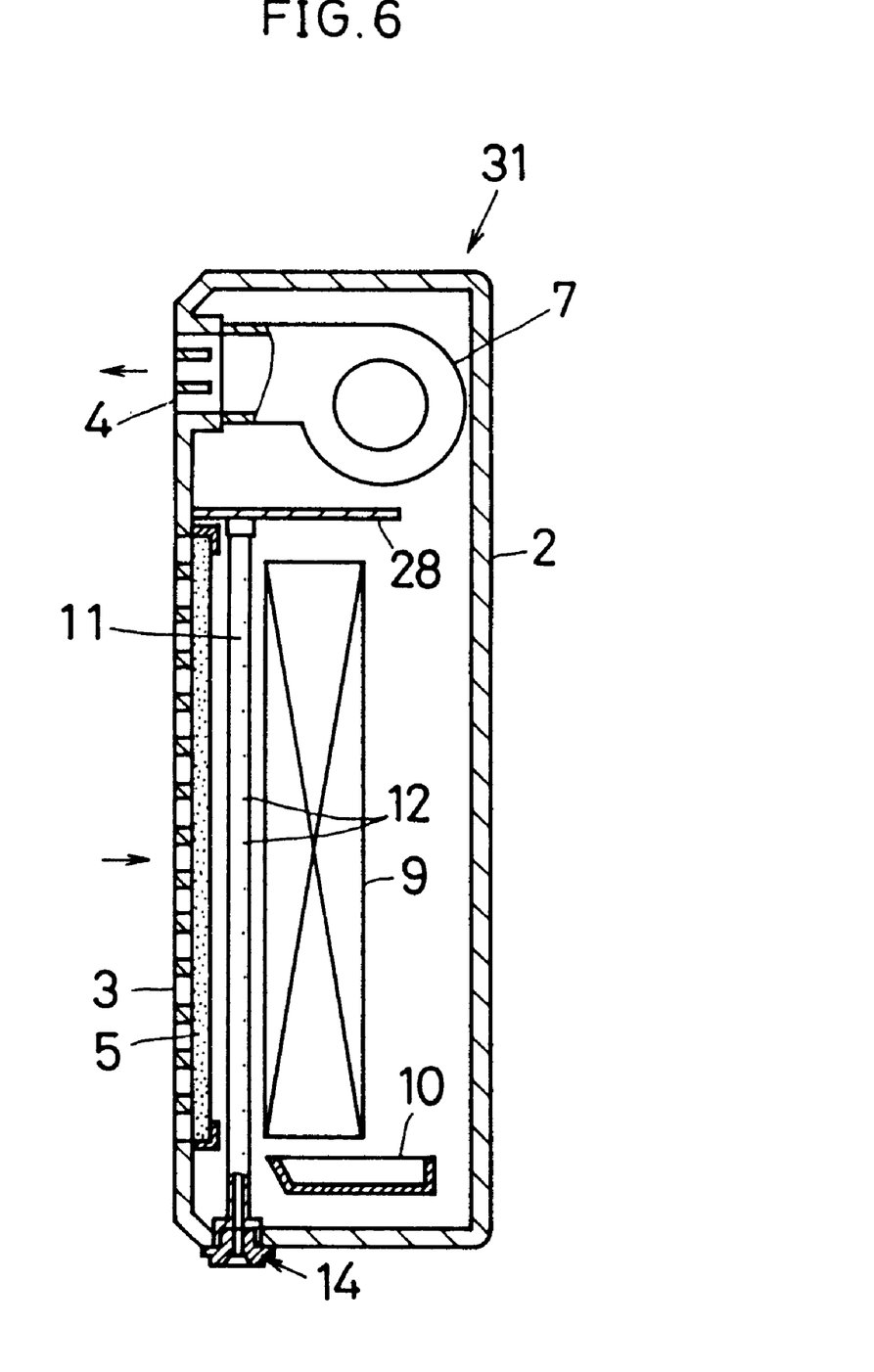
FIG. 6 is a sectional view showing other embodiment of the attachment to the wall mount type air-conditioner.

FIG. 6 shows an embodiment applied to a different type of wall mount air-conditioner 31, in which at least one nozzle 11 longer than the overall height of the heat exchanger 9 is disposed in the vertical direction between the upstream side of the heat exchanger 9 and the back side of the filter 5, and the basal end of the nozzle 11 and the receiving member 14 are coupled liquid tightly in the lower part of the housing 2, so that a piping-less structure is realized between the both members 11 and 14. In such constitution, nearly same actions and effects as in the foregoing embodiments are obtained.

Figure 7:
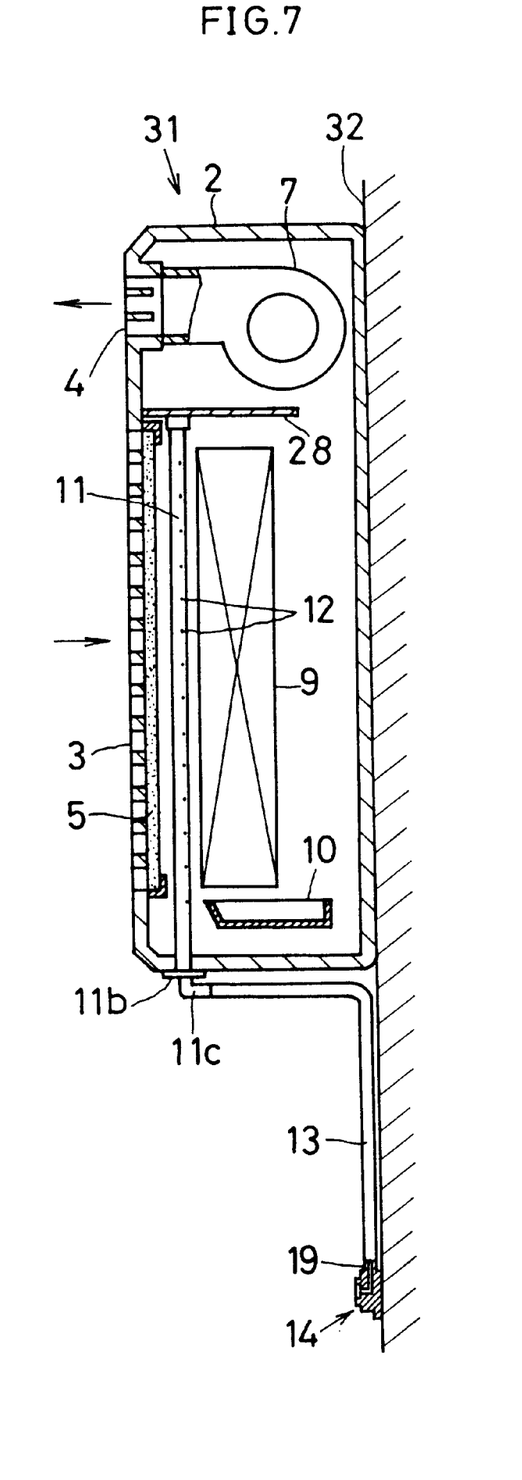
FIG. 7 is a sectional view showing other embodiment of receiving means mounting structure.

FIG. 7 refers to the same air-conditioner 31 shown in FIG. 6, in which the receiving member 14 is attached to the indoor side of the wall 32, and the joint 11c at the basal end of the nozzle 11 and the joint 19 of the receiving member 14 are connected directly through a rubber hose 13 or piping.

In this constitution, since the receiving member 14 is disposed at a close position easy for supply of solvent, the controllability of solvent supply from the solvent source (filling container A) can be substantially enhanced without sacrificing the appearance of the wall 32 of the indoor side of the building. Herein, the rubber hose 13 or at least part of the piping may be buried in the wall 32. In other points, nearly same actions and effects as in the foregoing embodiments are obtained.

Figure 8:
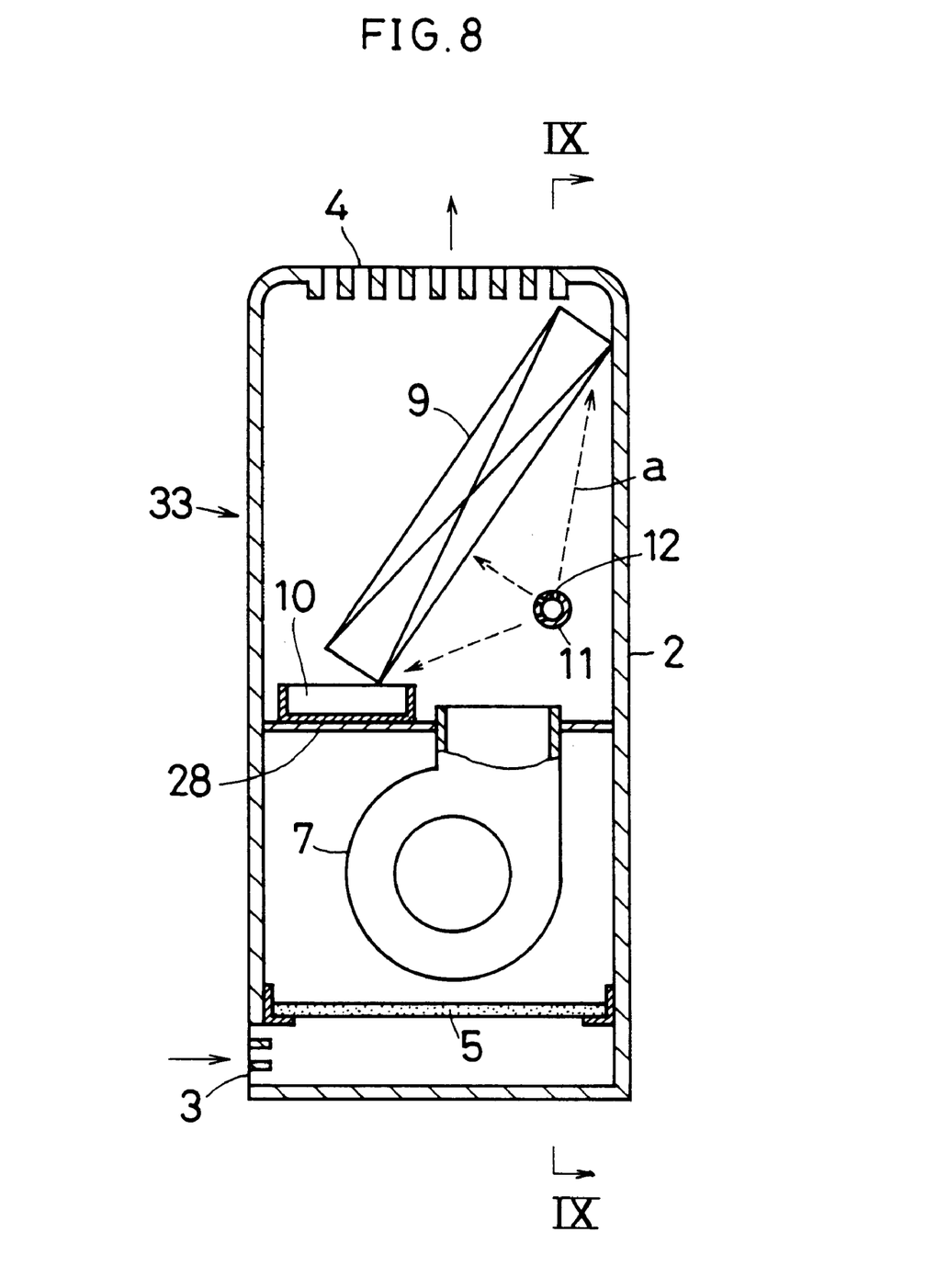
FIG. 8 is a sectional view showing an attachment to a stationary type air-conditioner of the invention.
Figure 9:
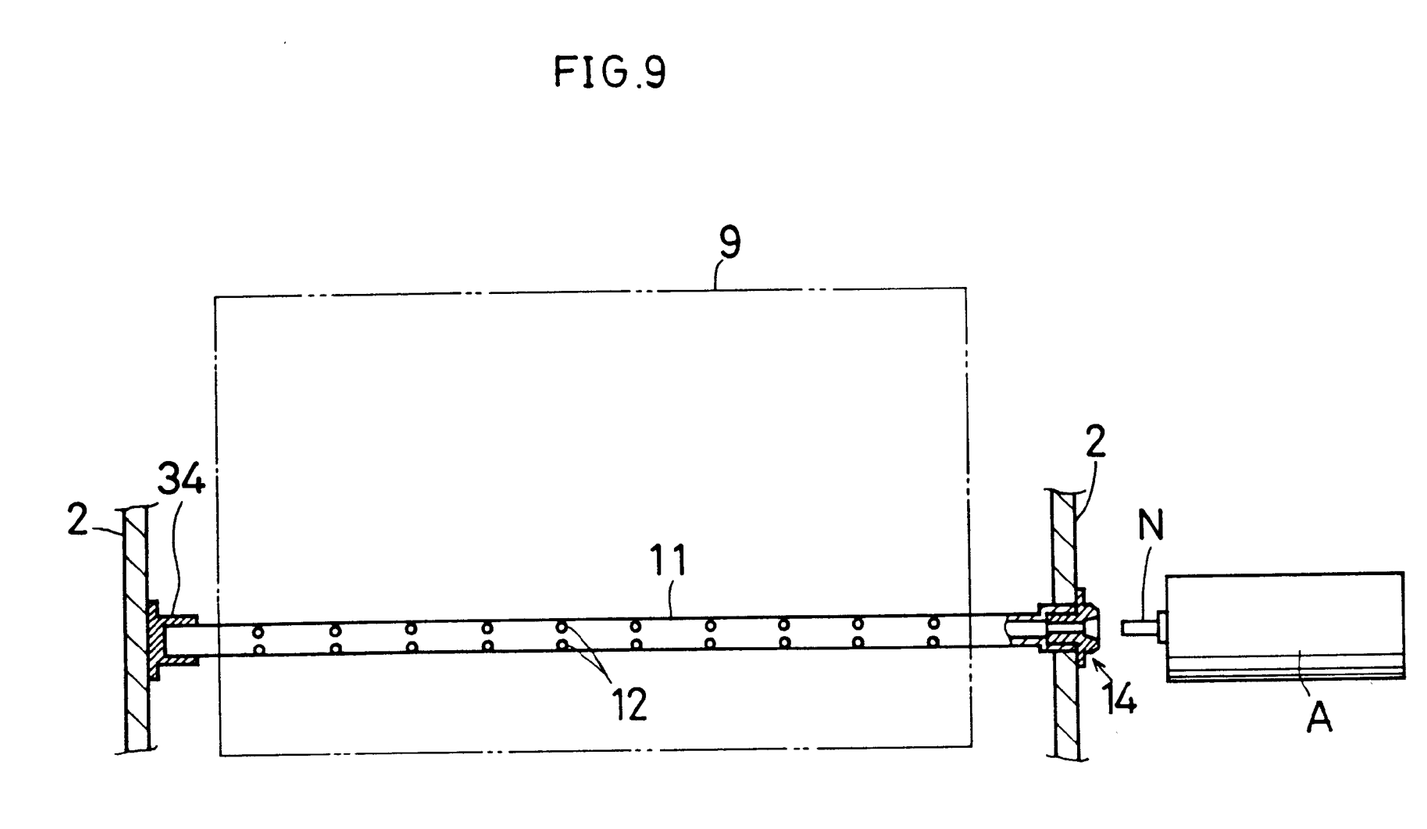
FIG. 9 is an essential magnified sectional view along line IX—IX in FIG. 8.
Figure 10:
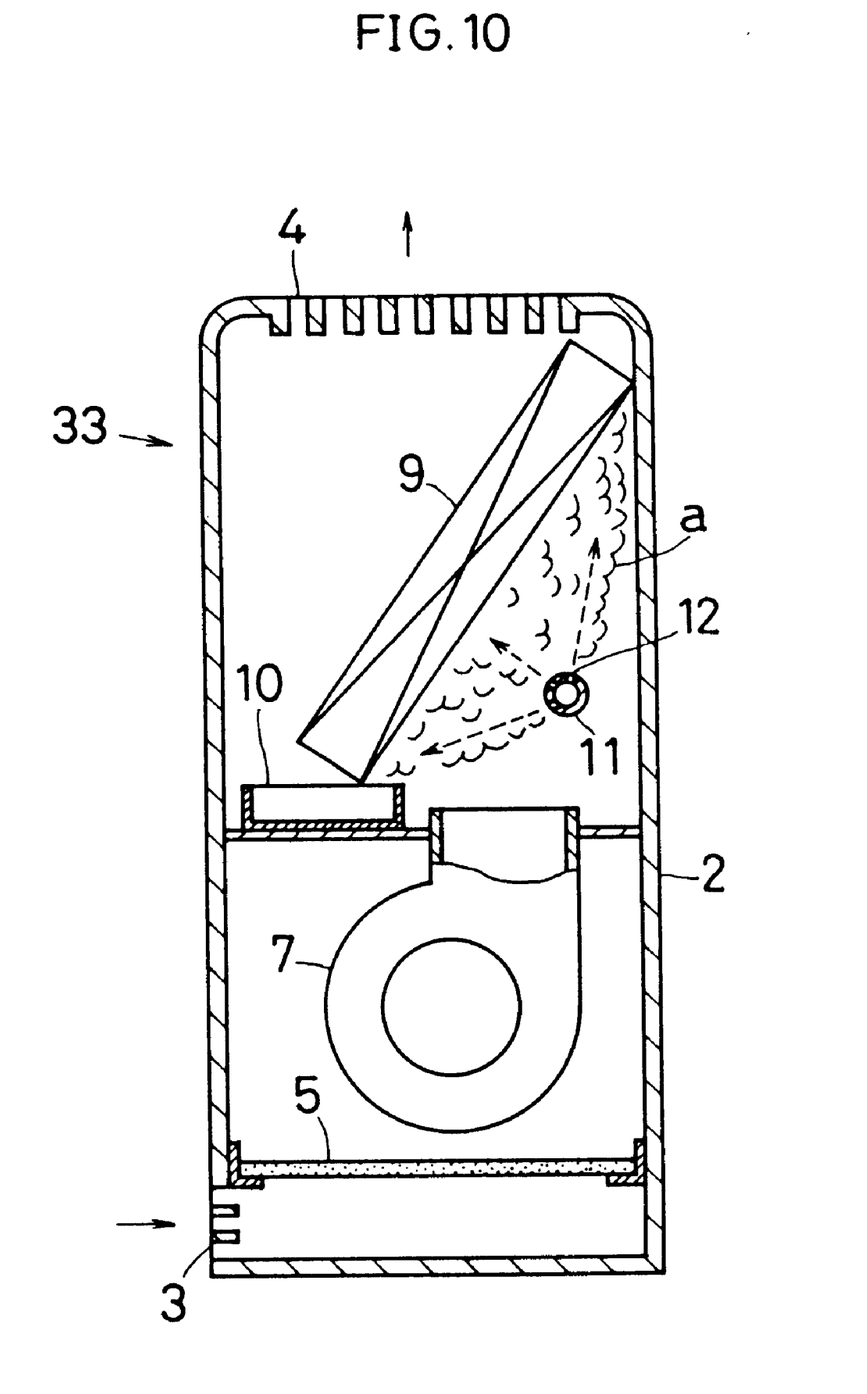
FIG. 10 is an explanatory diagram for using foamed cleaning fluid.

FIG. 8 and FIG. 9 show embodiments applied to a stationary air-conditioner 33, in which at least one nozzle 11 longer than the overall width of the heat exchanger 9 is disposed horizontally at the upstream side of the heat exchanger 9 the basal end of the nozzle 11 and the receiving member 14 are directly coupled liquid tightly at the side of the housing 2, and a piping-less structure is realized between the two members 11 and 14, while the leading end of the nozzle 11 is stably supported by a holder 34 made of synthetic resin or the like. In this constitution, too, nearly same actions and effects as in the foregoing embodiments are obtained, and further by setting the solvent fluid to be ejected from the nozzle 11 as foamed cleaning fluid as shown in FIG. 10, if the nozzle 11 is formed small and compact, the foamed cleaning fluid ejected from the nozzle 11 spreads over the entire heat exchanger 9 by its characteristic, thereby cleaning effectively deep into the inner parts.

Figure 11:
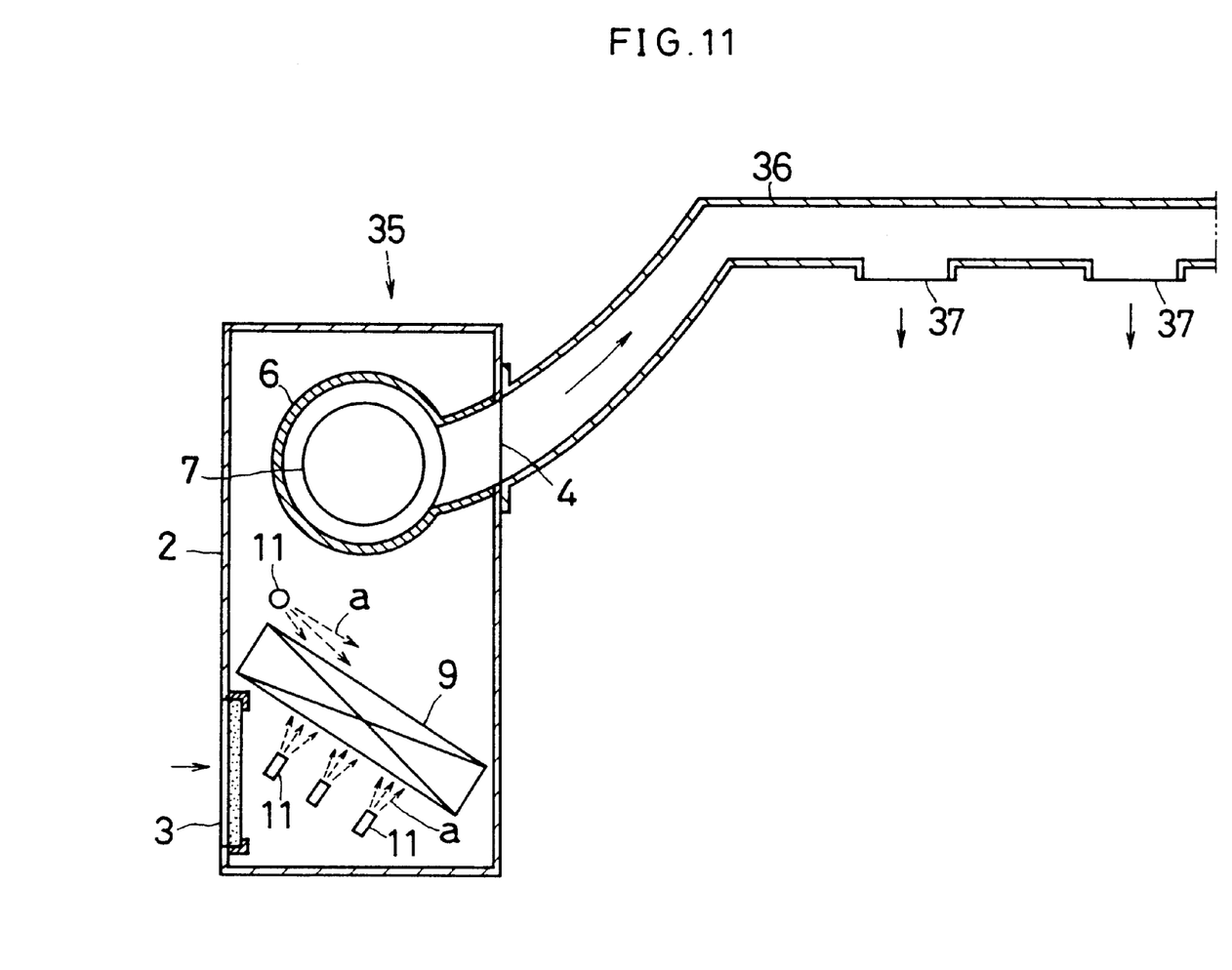
FIG. 11 is a sectional view showing an attachment to a box type air-conditioner.

FIG. 11 shows an embodiment applied to a box type air-conditioner 35, and in this air-conditioner 35, the air blow-out port 4 communicates with an air blow-out duct 36, and at least one air blow-out port 37 is opened in the duct 36, corresponding to each room.

A total of three nozzles 11 are disposed at the upstream side of the heat exchanger 9, and at the downstream side of the heat exchanger 9 and at its inclined upper end side, moreover, one nozzle 11 is disposed, and these nozzles 11 communicate with the receiving member 14 (not shown).

When ejecting the solvent from the nozzle 11 disposed at the upstream side of the heat exchanger 9, it is same as in the preceding embodiments, but when using the nozzle 11 at the inclined upper end side of the heat exchanger 9, the fan 7 is stopped, and the foamed cleaning fluid is ejected from this nozzle 11.

Since the foamed cleaning fluid sequentially flows downward by the inclination angle of the heat exchanger 9, the entire heat exchanger 9 can be cleaned effectively. When releasing an aromatic solvent into the room, the nozzle 11 may be located anywhere in the air-conditioning channel between the air suction port 3 and air blow-out port 37. In the embodiment shown in FIG. 11, too, in other points, nearly same actions and effects as in the foregoing embodiments are obtained.

Figure 12:
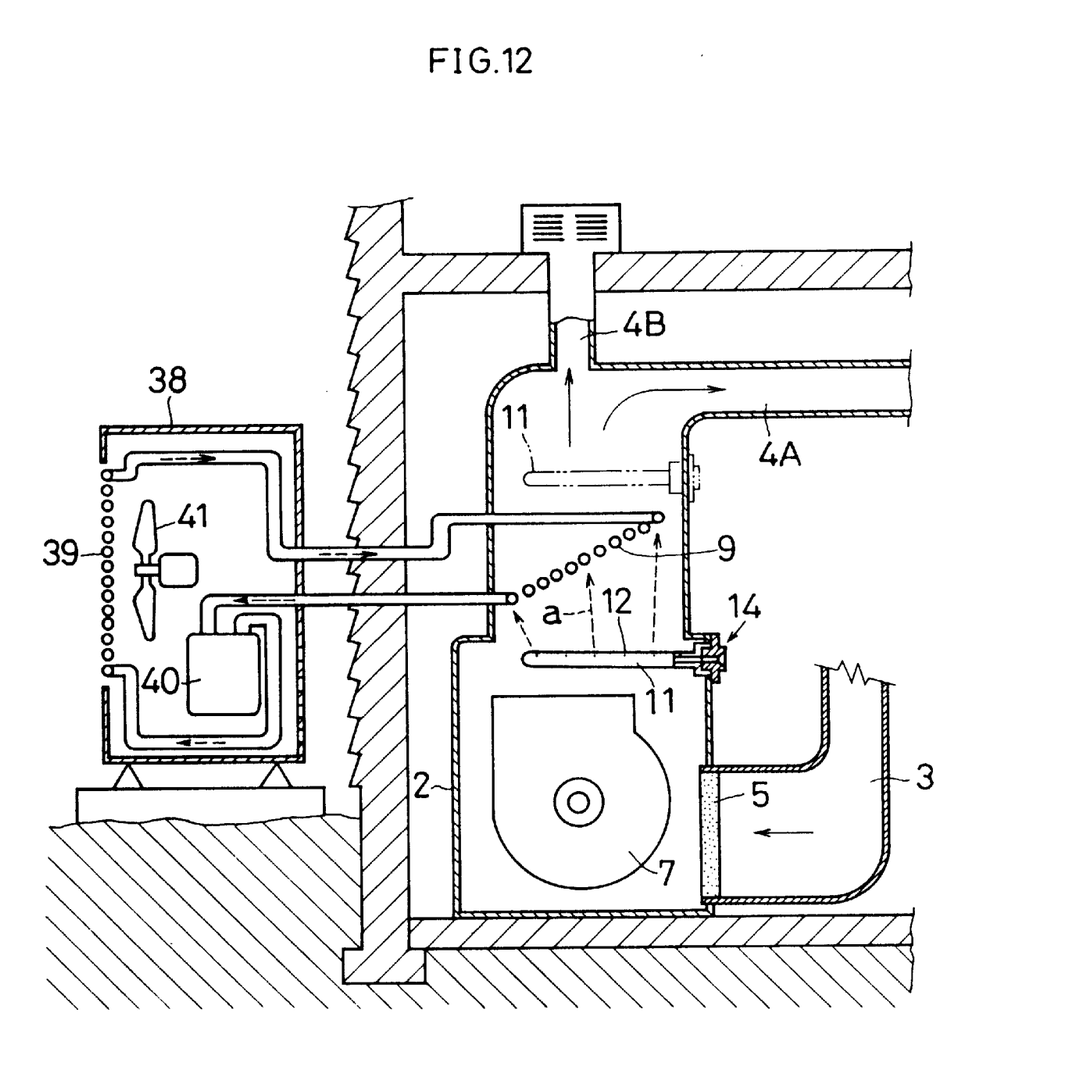
FIG. 12 is a sectional view showing an attachment to a central air-conditioning system.

FIG. 12 shows an embodiment applied to a central air-conditioning system, in which a nozzle 11 is horizontally laid at the upstream side of the heat exchanger 9 of the indoor unit, and the nozzle 11 is directly coupled with the receiving member 14. When driving the fan 7, cleaning, antimicrobial, deodorizing or anti-mold treatment can be applied nearly to the entire heat exchanger 9 by various solvents ejected from the ejection port 12 of the nozzle 11, and when using an aromatic solvent, aroma is released into the room through air blow-out ports 4A, 4B.

Moreover, by disposing nozzles 11 . . . at the upstream position of the air blow-out ports 4A, 4B, . . . for distributing and supplying air-conditioning wind into individual rooms respectively as indicated by virtual lines in FIG. 12, and using for duct cleaning, a favorable cleaning effect is obtained if the duct is long. Or, when using the nozzle 11 exclusively for aroma, as indicated by virtual line in FIG. 12, it may be disposed at the downstream side of the heat exchanger 9. In FIG. 12, meanwhile, reference numeral 38 is an outdoor unit comprising an outdoor side heat exchanger 39, a compressor 40, and a fan 41. In this constitution, too, nearly same actions and effects as in the foregoing embodiments are obtained.

In short, in the attachment in the embodiments, since at least one nozzle 11 as solvent discharge means is disposed at the upstream side (windward side) of the heat exchanger 9 or at the upper side of the location of t e heat exchanger 9 (see FIG. 11), effective cleaning, antifungal (including decontaminant, antimicrobial and bactericidal), deodorant (including odor preventive and odor removing) effect or anti-mold treatment can be applied nearly to the entire fins of complicated shape of the heat exchanger 9 where contamination is most likely to occur, and moreover aroma can be released into the room by making use of air-conditioning wind, and further when using a deodorant solvent, it is effective to deodorize not only the inside of the air-conditioner but also the room in which the air-conditioning wind is blown.

Herein, the nozzle 11 may be either long or short, and its material may be synthetic resin or metal, and its position of installation may be in any one of horizontal direction, vertical direction and slant direction, and the number of pieces may be one or a plurality. The ejection port 12 opened in the nozzle 11 may be of twin structure, and the opening direction may be oriented to both the heat exchanger 9 side and fan 6 side.

When using a plurality of nozzles 11, they may be disposed parallel at one location, or may be disposed at different locations at the upstream side of the heat exchanger and upstream side of the fan.

In correspondence between the constitution of the invention and the foregoing embodiments,

- air suction portion of the invention corresponds to the air suction port 3 in the embodiments, and similarly,
- the air blow-out portion, to the air blow-out port 4 or air blow-out port 37 at the leading end of the air blow-out duct 36,
- the solvent discharge means, to the nozzle 11,
- the solvent source, to the filling container A,
- the receiving means, to the receiving member 14, and
- the building and its indoor side, to the ceiling 25 and wall 32,
- but it must be noted that the invention is not limited to the constitution of the embodiments only.

For example, when mounting the receiving member 14 on the indoor side, at least part of the solvent feed route (rubber hose 13) may be buried in the wall, and the solvent feed route provided at the indoor side may be enclosed by, for example, a cover member of a recess section.

What is claimed is:

1. An attachment for an air-conditioner comprising discharge means positioned inside said air-conditioner and between an air suction portion of said air-conditioner and an air blow out portion of said air-conditioner, said discharge means receiving a solvent from a solvent source and discharging said solvent in said air-conditioner, wherein said discharge means comprises:

a hollow cylindrical tube having a closed first end and an open second end with a plurality of holes in at least one direction thereof, and further comprising means for connecting said second end to said solvent source so that the solvent from the solvent source is discharged through said plurality of holes in the at least one direction into the air-conditioner between the air suction portion and the blow out portion, and wherein the solvent is selected from the group consisting of cleaning solvent, aromatic solvent, anti-microbial solvent, deodorant solvent, and anti-mold solvent.

2. The attachment of claim 1, wherein said discharge means is positioned at an upstream side of a heat exchanger of said air-conditioner.

3. The attachment of claim 1, wherein said means for connecting is disposed on an outer surface of said air-conditioner.

4. The attachment of claim 3, wherein said discharge means is positioned at an upstream side of a heat exchanger of said air-conditioner.

5. The attachment of claim 4, wherein said discharge means is disposed parallel with the heat exchanger.

6. The attachment of claim 1, wherein said means for connecting is disposed on an indoor side surface of a building to which said air-conditioner is attached.

7. The attachment of claim 1, wherein said discharge means is positioned at a downstream side of a heat exchanger of said air-conditioner.

8. The attachment of claim 1, wherein said discharge means is positioned on both the upstream and downstream sides of a heat exchanger of said air-conditioner.

* * * * *